United States Patent
Ishizaki et al.

(10) Patent No.: US 10,729,838 B2
(45) Date of Patent: Aug. 4, 2020

(54) BLOOD PURIFICATION APPARATUS

(71) Applicant: Nikkiso Company Limited, Tokyo (JP)

(72) Inventors: Fumihiko Ishizaki, Shizuoka (JP); Shinya Hasegawa, Shizuoka (JP); Yuki Obata, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 15/946,856

(22) Filed: Apr. 6, 2018

(65) Prior Publication Data

US 2018/0221556 A1     Aug. 9, 2018

Related U.S. Application Data

(63) Continuation of application No. PCT/JP2016/080187, filed on Oct. 12, 2016.

(30) Foreign Application Priority Data

Oct. 13, 2015 (JP) .................... 2015-201891

(51) Int. Cl.
  *A61M 1/16* (2006.01)
  *A61L 2/04* (2006.01)
  *A61L 2/18* (2006.01)

(52) U.S. Cl.
  CPC ............ *A61M 1/1686* (2013.01); *A61L 2/04* (2013.01); *A61L 2/18* (2013.01); *A61M 1/16* (2013.01);
  (Continued)

(58) Field of Classification Search
  CPC ... A61L 2/04; A61L 2/18; A61M 1/16; A61M 1/1629; A61M 1/165; A61M 1/1656;
  (Continued)

(56) References Cited

U.S. PATENT DOCUMENTS 6,153,102 A     11/2000 Kenley et al.
2014/0183114 A1*     7/2014 Iwahori ................. A61M 1/168
                                                    210/175
(Continued)

FOREIGN PATENT DOCUMENTS

JP     2014-097197     5/2014

OTHER PUBLICATIONS

International Search Report from the Japanese Patent Office for Application No. PCT/JP2016/080187 dated Dec. 6, 2016.
(Continued)

*Primary Examiner* — Dirk R Bass
(74) *Attorney, Agent, or Firm* — Young Basile Hanlon & MacFarlane, P.C.

(57) ABSTRACT

To provide a blood purification apparatus in which the hot-water-disinfection time can be optimized with consideration for environmental conditions. A blood purification apparatus provided with a dialyzer for giving dialysis treatment to a patient, and with a tube for introducing dialysate into or discharging drain liquid from the dialyzer. The apparatus includes a thermistor that is capable of detecting an environmental condition at a time of a hot-water-disinfection process in which the tube is disinfected with hot water or a parameter regarding the environmental condition, and an estimating device that estimates a hot-water-disinfection time required for the hot-water disinfection of the tube in accordance with the environmental condition or the parameter regarding the environmental condition detected by thermistor.

19 Claims, 10 Drawing Sheets

(52) U.S. Cl.
CPC .......... *A61M 1/165* (2014.02); *A61M 1/1629* (2014.02); *A61M 1/1688* (2014.02); *A61M 1/1656* (2013.01); *A61M 2202/0413* (2013.01); *A61M 2205/3327* (2013.01); *A61M 2205/3331* (2013.01); *A61M 2205/3368* (2013.01); *A61M 2205/36* (2013.01); *A61M 2205/50* (2013.01)

(58) Field of Classification Search
CPC .............. A61M 1/1686; A61M 1/1688; A61M 2202/0413; A61M 2205/3327; A61M 2205/3331; A61M 2205/3368; A61M 2205/36; A61M 2205/50
See application file for complete search history.

(56) References Cited

U.S. PATENT DOCUMENTS

2015/0021245 A1  1/2015  Rohde et al.
2015/0273090 A1* 10/2015  Felding ............... A61M 1/1686
                                                             210/149

OTHER PUBLICATIONS

Extended European Search Report dated Jan. 4, 2019, Application No. 16855406.1.

* cited by examiner

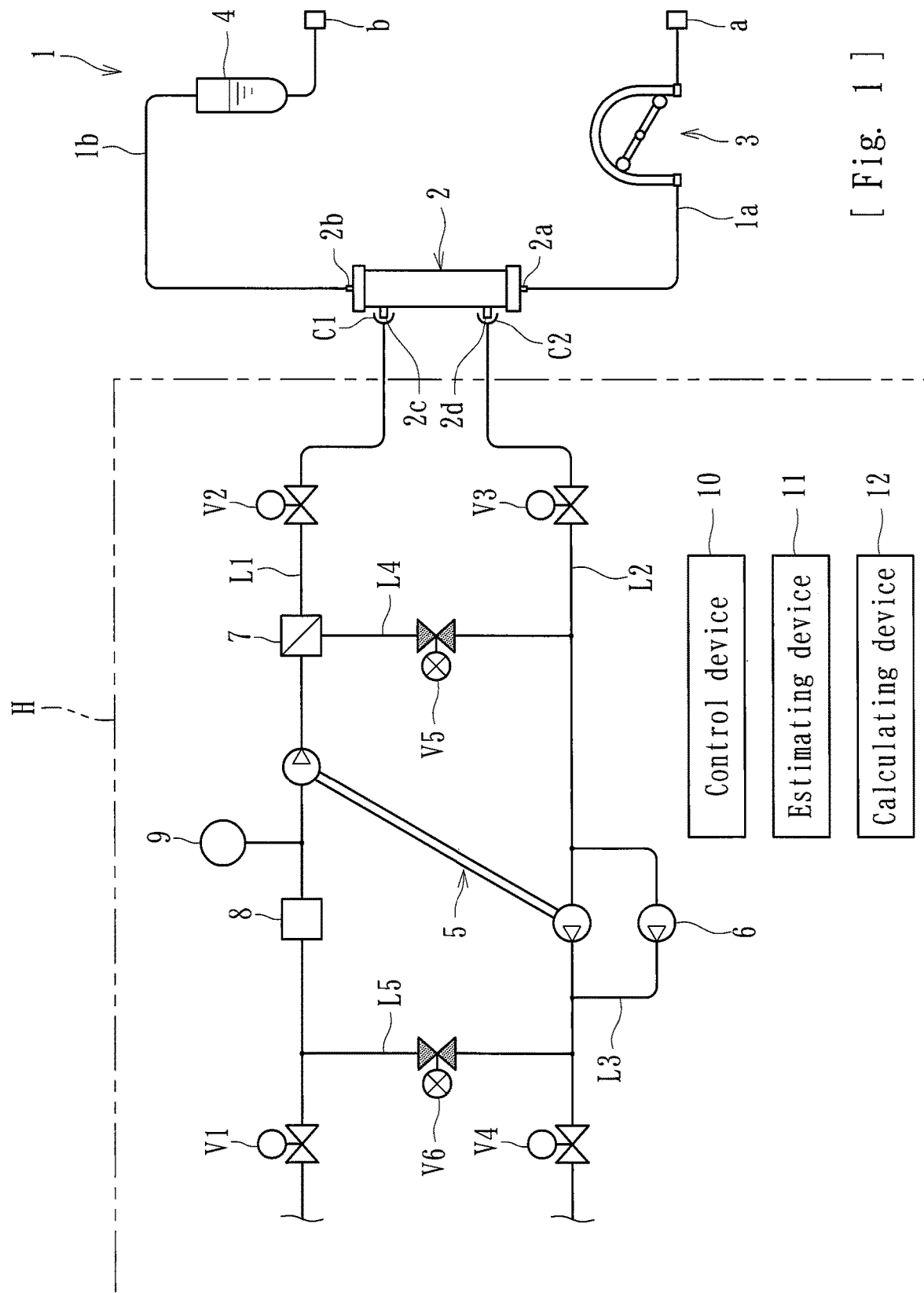
[Fig. 1]

[Fig. 2]
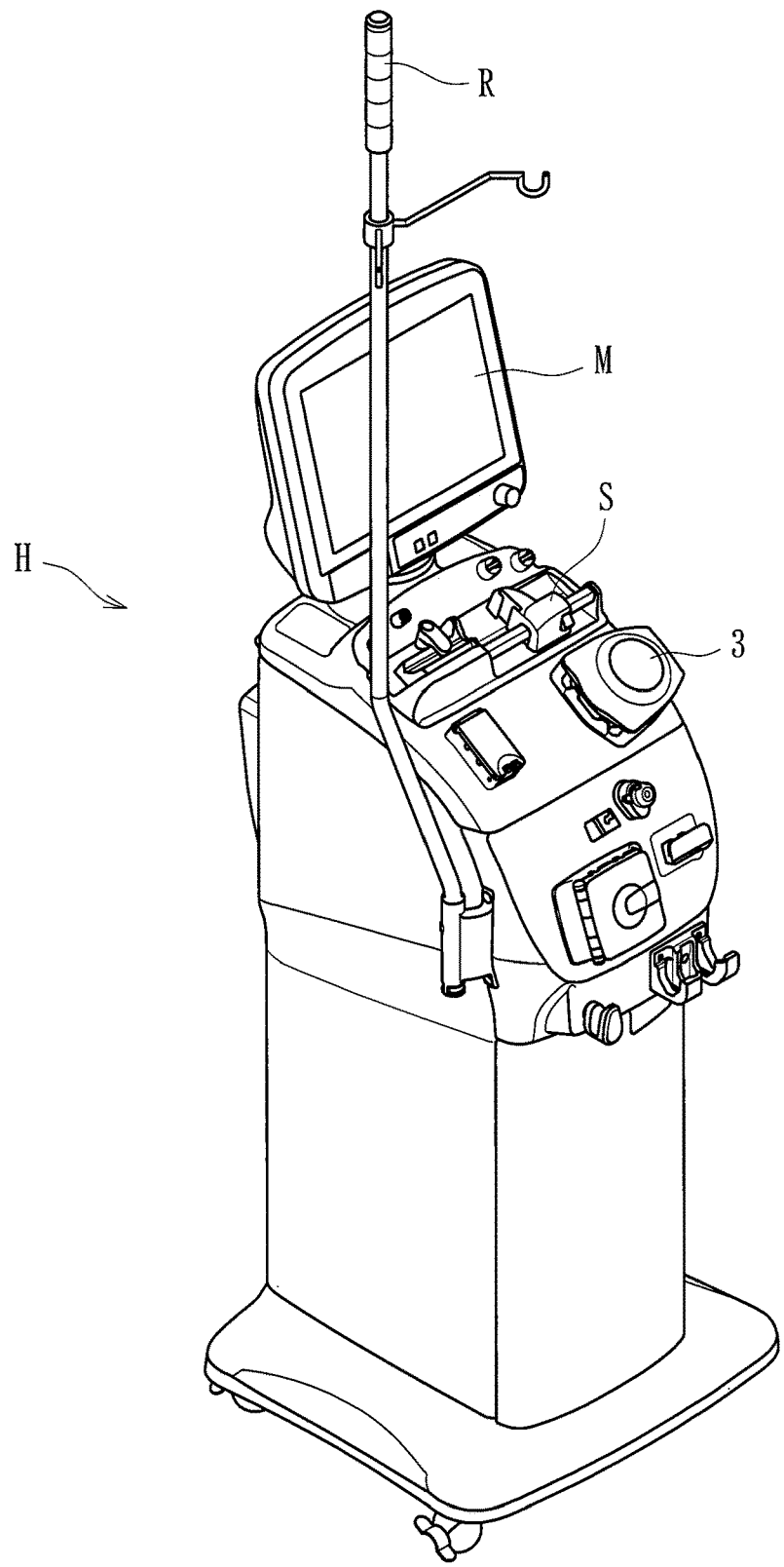

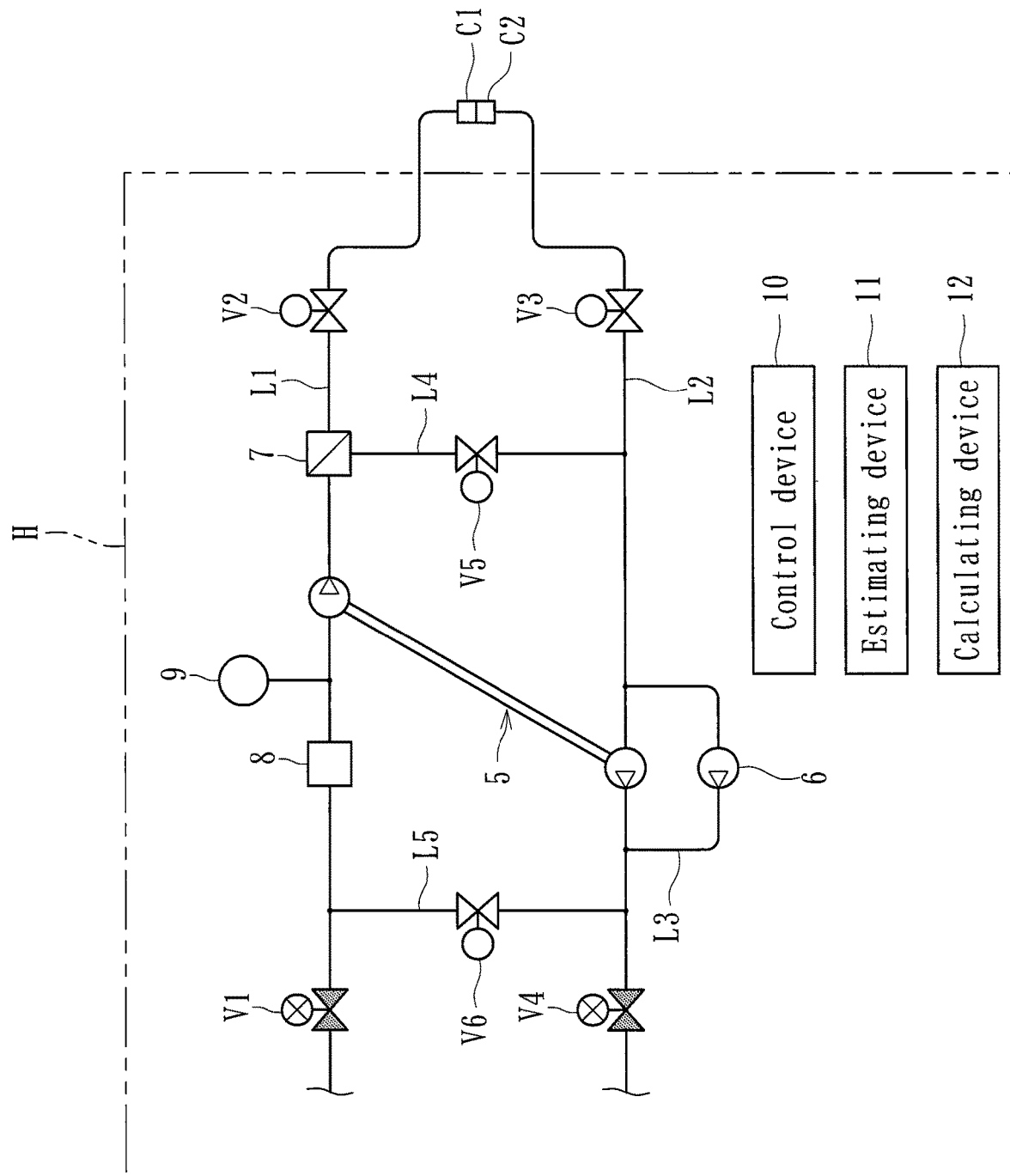
[Fig. 3]

| Power-source voltage | Supply water temperature | Ambient temperature | Time elapsed before temperature rises to X°C | Degree of temperature rise in X minutes | Washing-disinfection time |
|---|---|---|---|---|---|
| Upper-limit voltage | Upper-limit liquid temperature | Upper-limit room temperature | A minutes or shorter | A value or smaller | XX minutes |
| Upper-limit voltage | Upper-limit liquid temperature | Lower-limit room temperature | A to B minutes | A to B value | XX minutes |
| Upper-limit voltage | Lower-limit liquid temperature | Upper-limit room temperature | B to C minutes | B to C value | XX minutes |
| Upper-limit voltage | Lower-limit liquid temperature | Lower-limit room temperature | C to D minutes | C to D value | XX minutes |
| Lower-limit voltage | Upper-limit liquid temperature | Upper-limit room temperature | D to E minutes | D to E value | XX minutes |
| Lower-limit voltage | Upper-limit liquid temperature | Lower-limit room temperature | E to F minutes | E to F value | XX minutes |
| Lower-limit voltage | Lower-limit liquid temperature | Upper-limit room temperature | F to G minutes | F to G value | XX minutes |
| Lower-limit voltage | Lower-limit liquid temperature | Lower-limit room temperature | G minutes or longer | G value or greater | XX minutes |
| XX voltage | XX liquid temperature | XX room temperature | X to Y minutes | X to Y value | XX minutes |
| XY voltage | XY liquid temperature | XY room temperature | Y to Z minutes | Y to Z value | XX minutes |

[ Fig. 4 ]

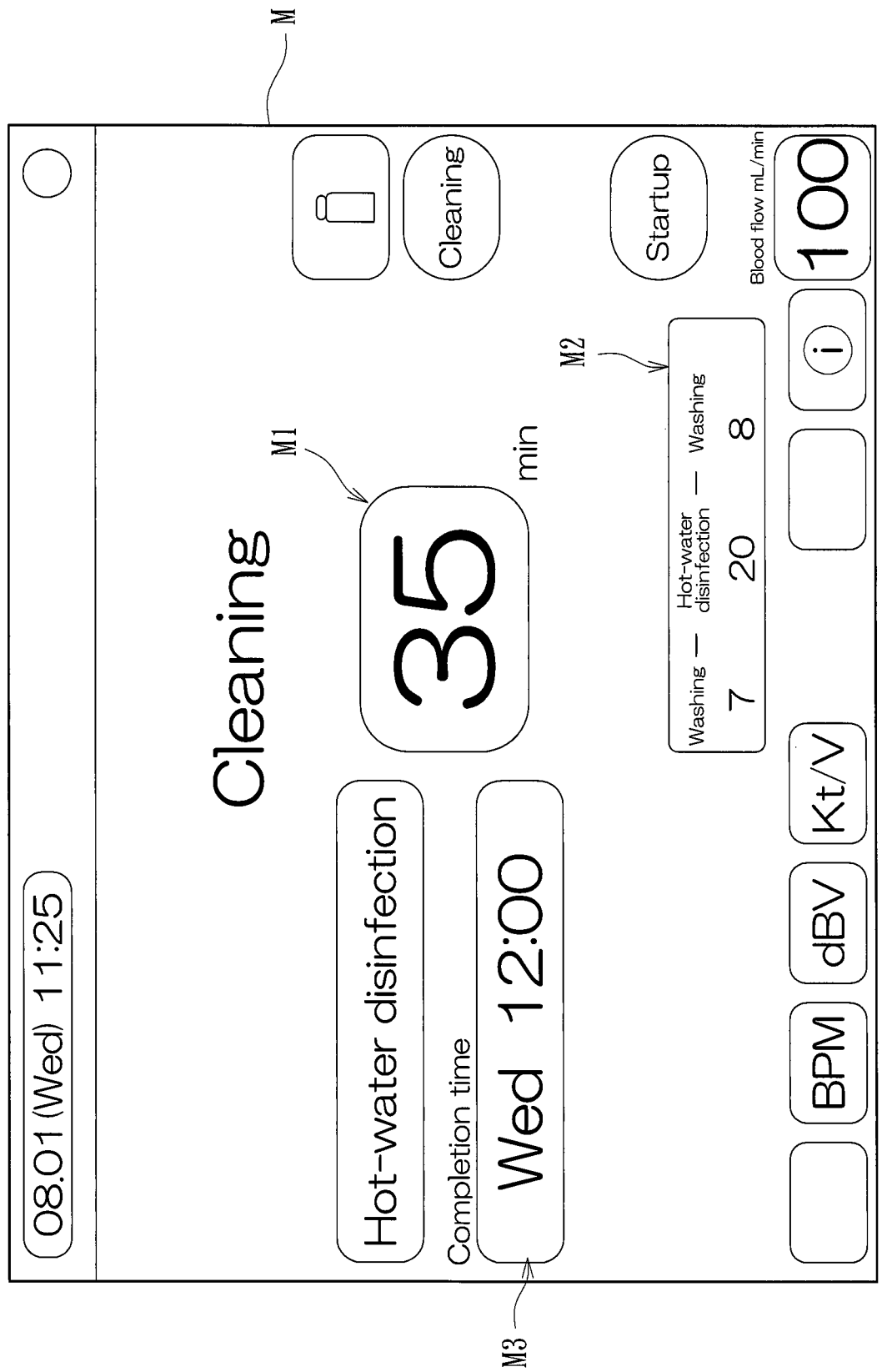
[Fig. 5]

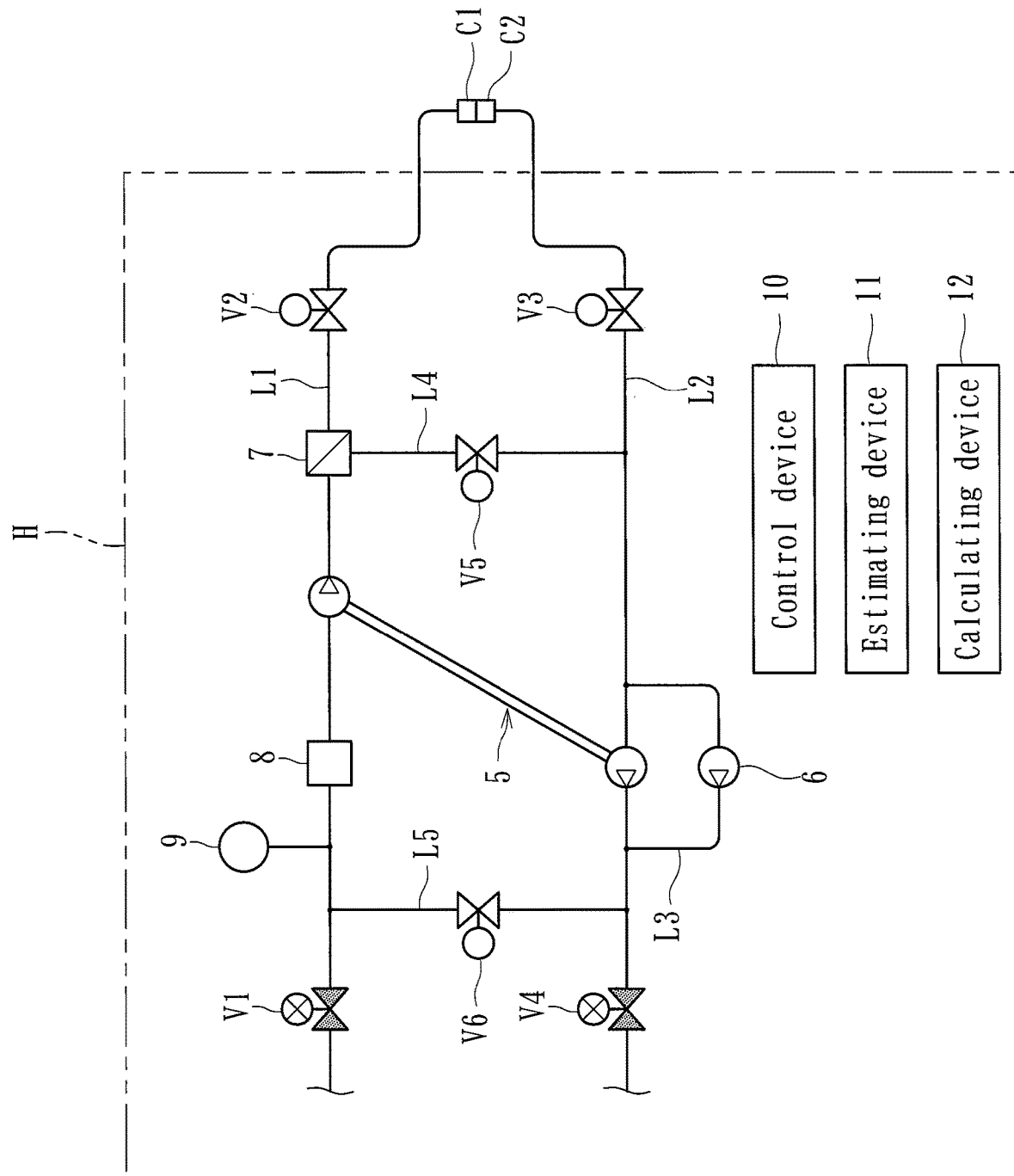
[Fig. 6]

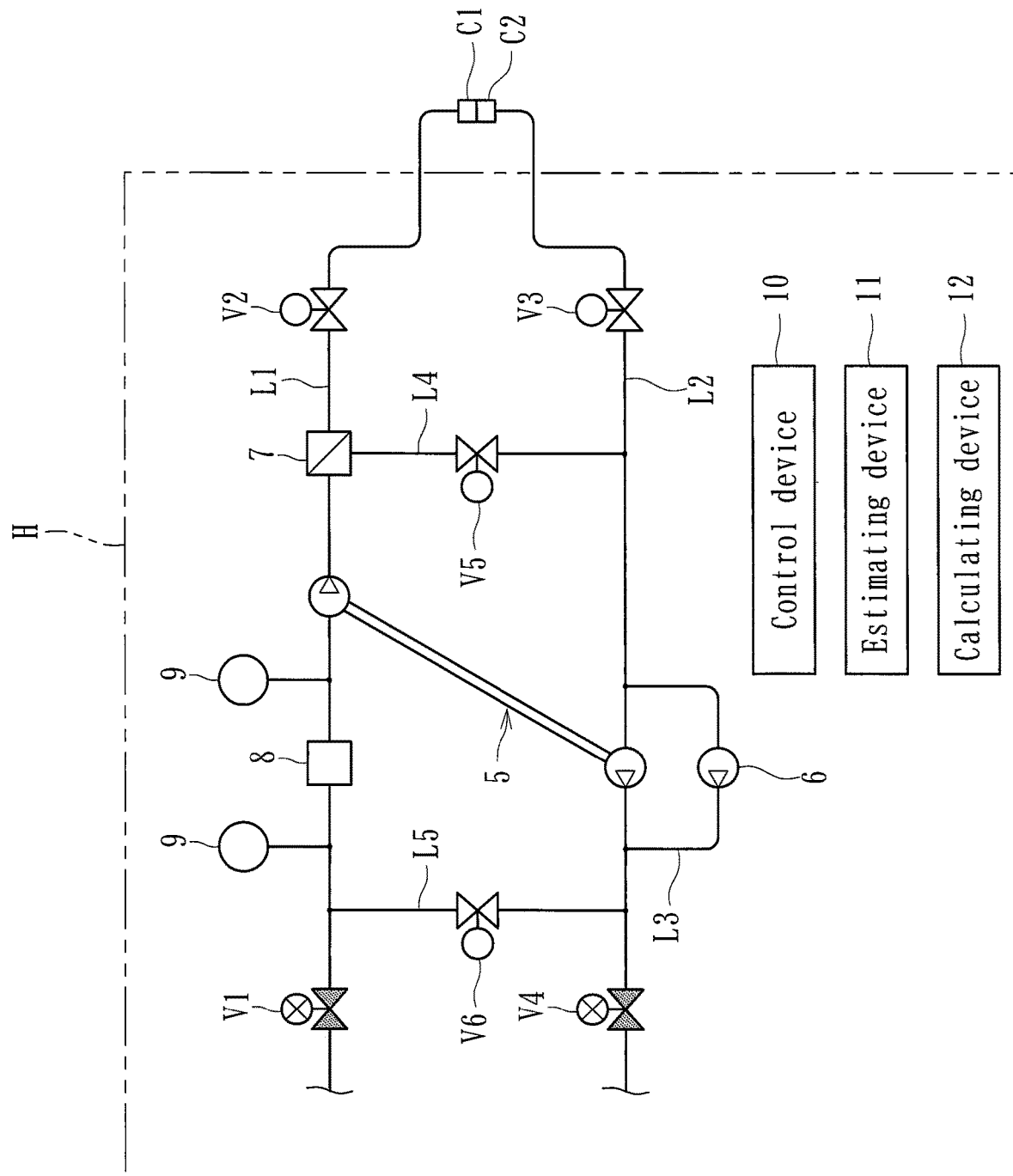
[Fig. 7]

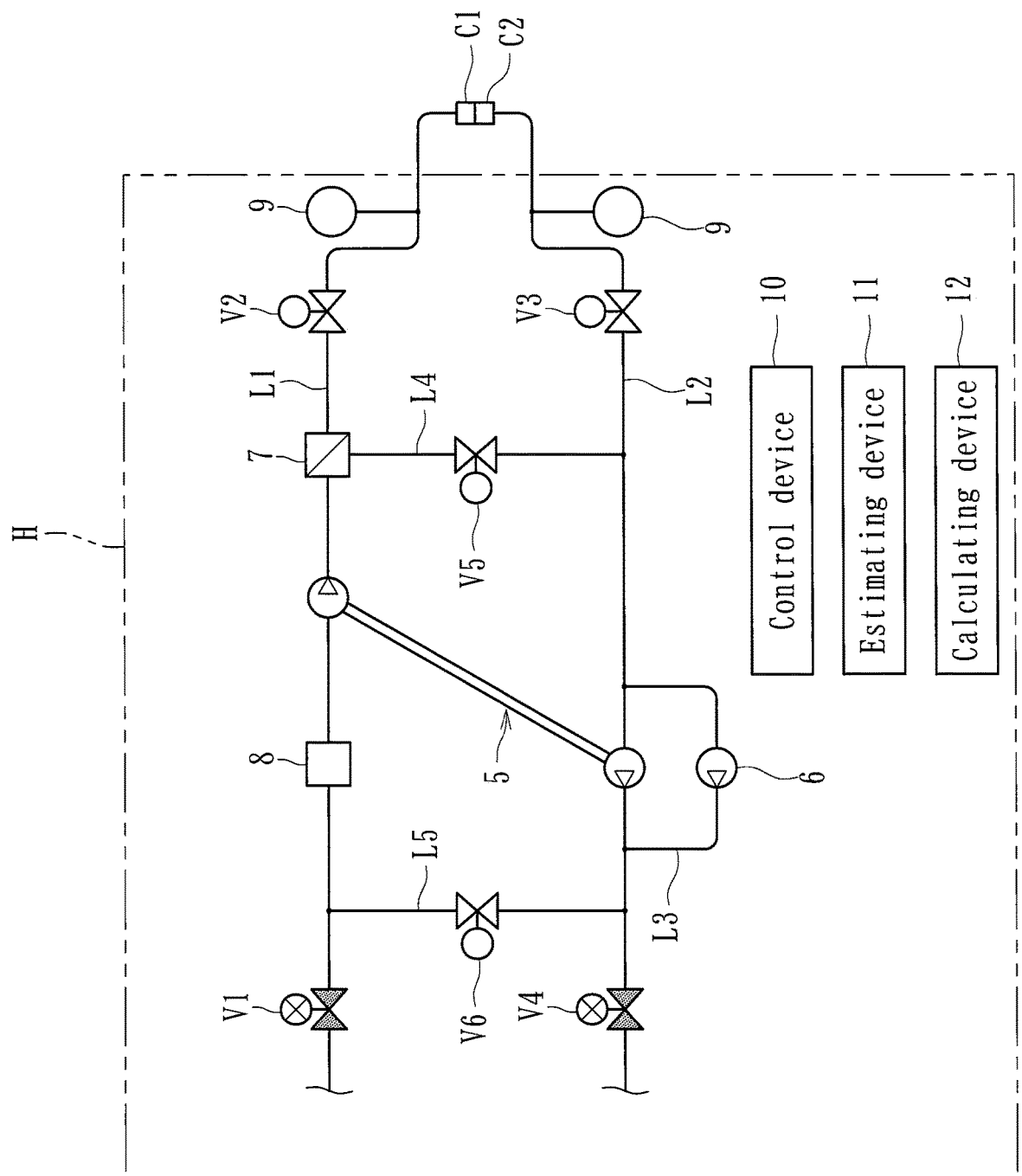
[Fig. 8]

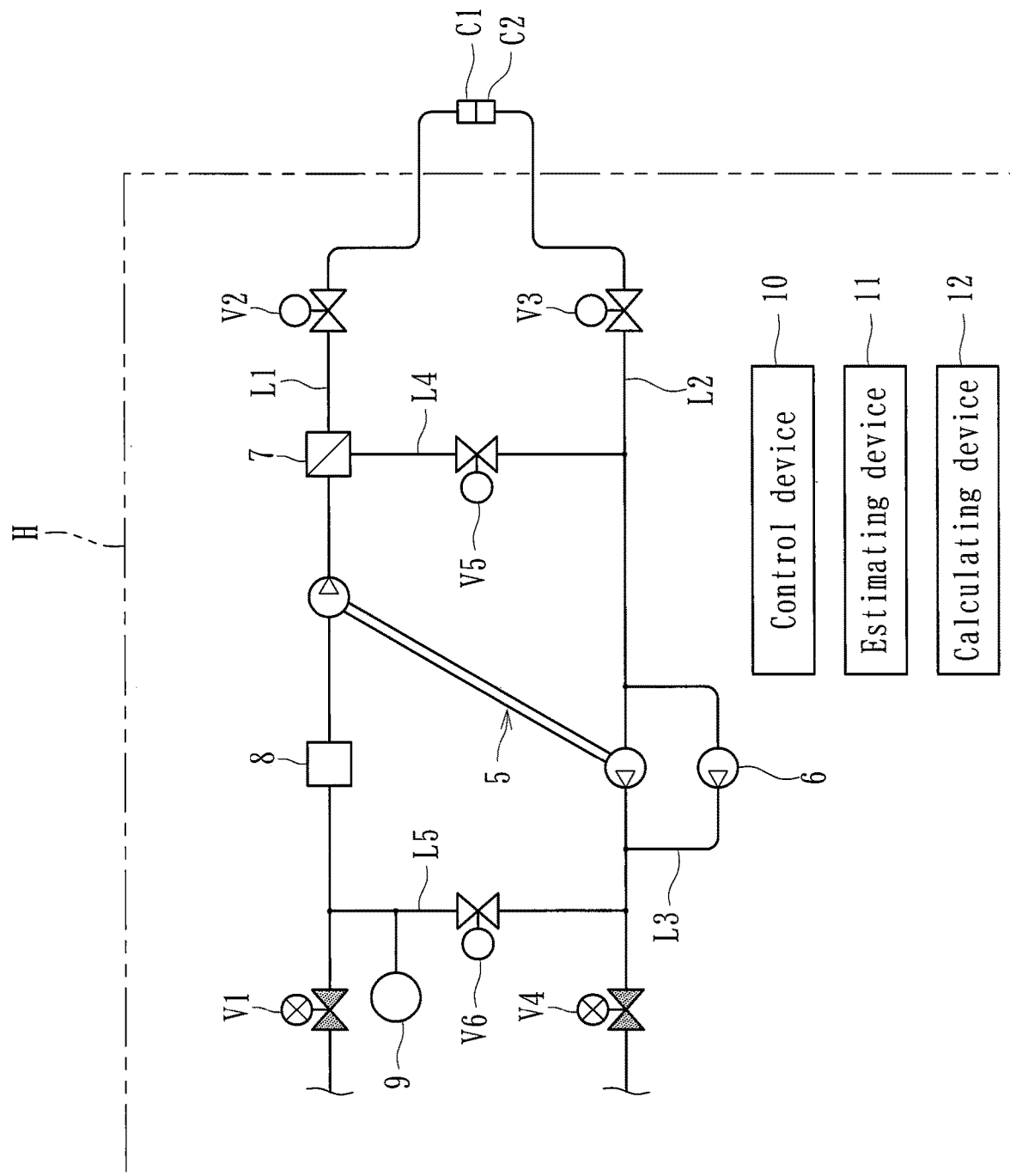
[Fig. 9]

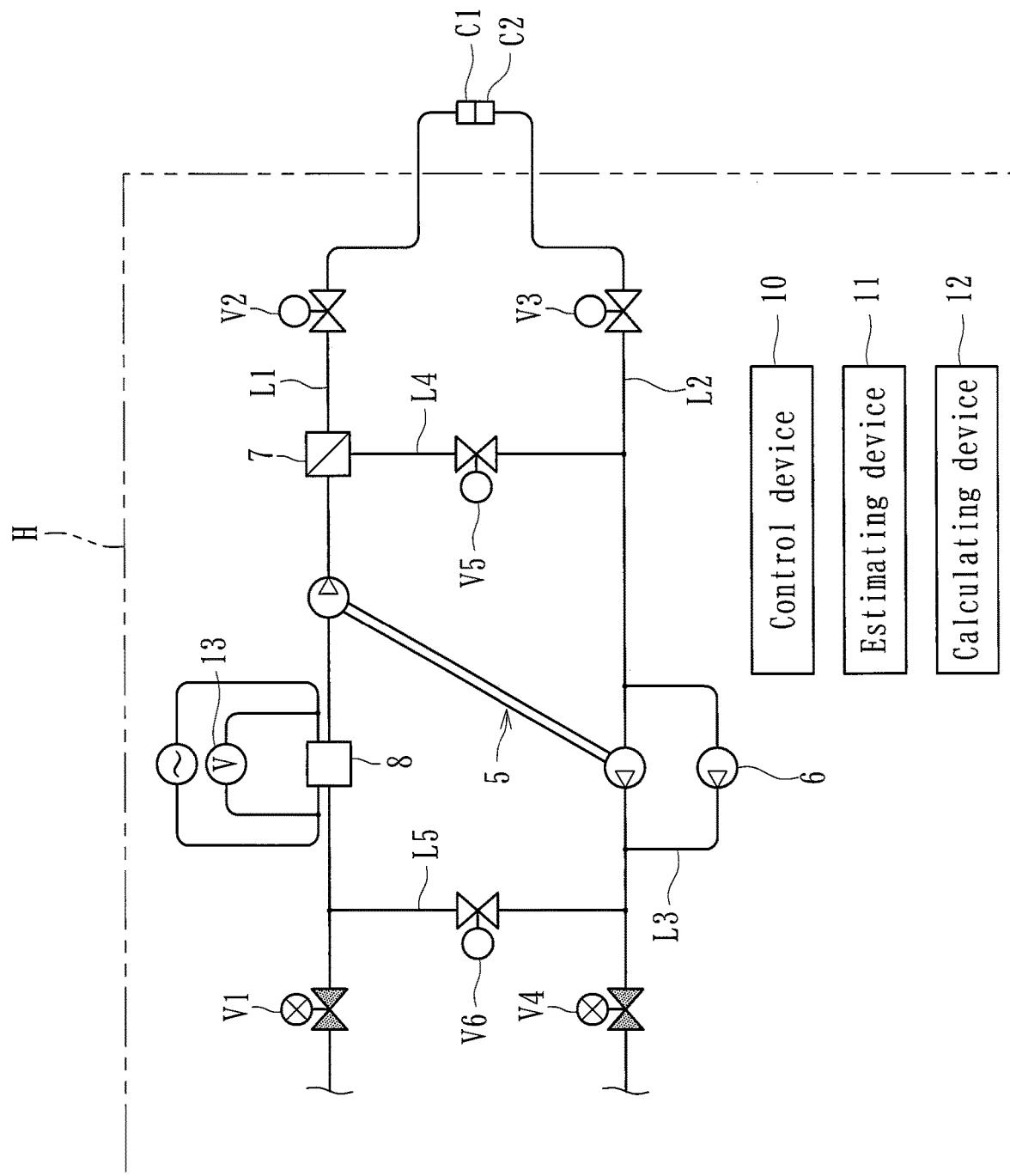
[Fig. 10]

BLOOD PURIFICATION APPARATUS

FIELD

The present teachings relate to a blood purification apparatus provided with a blood purification device for giving dialysis treatment to a patient, and with a tube for introducing dialysate into or discharging drain liquid from the blood purification device.

BACKGROUND

In general, a dialysis apparatus serving as a blood purification apparatus intended for dialysis treatment is provided with tubes, such as a dialysate introduction line and a dialysate drain line, for introducing dialysate into a dialyzer (a blood purification device) connected to a blood circuit and for discharging the dialysate containing waste products resulting from the dialysis from the dialyzer. The dialysate introduction line and the dialysate drain line are connected at the distal ends thereof to a dialysate inlet and a dialysate outlet, respectively, of the dialyzer. Furthermore, the dialysate introduction line is connected at the proximal end thereof to a dialysate-supplying device. Thus, the dialysate is allowed to be supplied to the dialyzer.

In such a blood purification apparatus, the tubes such as the dialysate introduction line and the dialysate drain line are disinfected by washing prior to the dialysis treatment. In recent years, a hot-water-disinfection process in which hot water (with citric acid) is used as a washing-and-disinfection solution has been becoming popular. As disclosed by PTL 1, for example, such a known blood purification apparatus includes a circulation tube for forming a circulation flow route that allows liquid (washing water) to circulate in the hot-water-disinfection process, a heater (a heating device) capable of heating the liquid that circulates through the circulation flow route and generating hot water that is at a temperature required for hot-water disinfection, and a thermistor (a temperature-measuring device) capable of measuring the temperature of the liquid heated by the heater. The tubes are disinfected with hot water by causing the hot water at a predetermined temperature to circulate through the circulation flow route for a period of time required for hot-water disinfection.

PTL 1: Japanese Unexamined Patent Application Publication No. 2014-097197

The above known blood purification apparatus has the following problem.

The hot-water disinfection of tubes greatly depends on environmental conditions at the time of the hot-water-disinfection process. Therefore, the hot-water-disinfection time and so forth are set such that a satisfactory level of disinfection effect can be obtained even under the worst environmental conditions. That is, assuming that environmental conditions, such as the heating function of the heater (the power-source voltage); the supply water temperature; and the ambient temperature, are all at the worst levels in terms of generating hot water suitable for hot-water disinfection, a long hot-water-disinfection time estimated for the worst conditions is set so that a satisfactory level of hot-water-disinfection effect is guaranteed.

However, the hot-water-disinfection time that is set as described above tends to be greatly different from the hot-water-disinfection time that is required under normal environmental conditions. Therefore, the hot-water-disinfection time thus set tends to be excessively long. That is, in the known technique, hot-water disinfection cannot be performed efficiently, which may increase the power consumption and the heat stress given to components such as filters provided to the tubes. Hence, to make the hot-water-disinfection process more efficient, the hot-water-disinfection time needs to be optimized with consideration for environmental conditions.

SUMMARY

The present teachings have been conceived in view of the above circumstances and provides a blood purification apparatus in which the hot-water-disinfection time can be optimized with consideration for environmental conditions.

According to the teachings herein, there is provided a blood purification apparatus provided with a blood purification device for giving dialysis treatment to a patient, and with a tube for introducing dialysate into or discharging drain liquid from the blood purification device. The apparatus includes a detecting device that is capable of detecting an environmental condition at a time of a hot-water-disinfection process in which the tube is disinfected with hot water or a parameter regarding the environmental condition, and an estimating device that estimates a hot-water-disinfection time required for the hot-water disinfection of the tube in accordance with the environmental condition or the parameter regarding the environmental condition detected by the detecting device.

According to the teachings herein, the blood purification apparatus taught herein further includes a calculating device that calculates, from the hot-water-disinfection time estimated by the estimating device, a completion time of the hot-water disinfection or a remaining time before a completion of the hot-water disinfection.

According to the teachings herein, the blood purification apparatus taught herein further includes a circulation tube for forming a circulation flow route that allows liquid to circulate in the hot-water-disinfection process, a heating device capable of heating the liquid circulating through the circulation flow route and generating hot water at a temperature required for hot-water disinfection, and a temperature-measuring device capable of measuring a temperature of the liquid heated by the heating device. The detecting device is the temperature-measuring device, and a value measured by the temperature-measuring device is the parameter regarding the environmental condition.

According to the teachings herein, in the blood purification apparatus taught herein, the heating device and the temperature-measuring device are provided to the circulation flow route.

According to the teachings herein, in the blood purification apparatus taught herein, the temperature-measuring device is provided on a downstream side of the heating device.

According to the teachings herein, in the blood purification apparatus taught herein, the temperature-measuring device is provided on the downstream side of and near the heating device.

According to the teachings herein, in the blood purification apparatus taught herein, the estimating device has a table created for obtaining the hot-water-disinfection time from the value measured by the temperature-measuring device. The table is prepared in accordance with a correlation, under a certain environmental condition, between the value measured by the temperature-measuring device and a temperature at a position of the circulation flow route that is on a downstream side of the temperature-measuring device and on the upstream side of the heating device.

According to the teachings herein, in the blood purification apparatus taught herein, the estimating device has a table created for obtaining the hot-water-disinfection time from the value measured by the temperature-measuring device. The table is prepared in accordance with a correlation, under a certain environmental condition, between the value measured by the temperature-measuring device and a temperature at a position of the circulation flow route that is on a downstream side of the temperature-measuring device and on the upstream side of and near the heating device.

According to the teachings herein, in the blood purification apparatus taught herein, the estimating device has a table created for obtaining the hot-water-disinfection time from the value measured by the temperature-measuring device. The table is prepared in accordance with a correlation, under a certain environmental condition, between the value measured by the temperature-measuring device and a temperature at a position of the circulation flow route where a rise of the temperature with the heating by the heating device is slow.

According to the teachings herein, in the blood purification apparatus taught herein, at least one of the environmental conditions summarized in the table is identifiable from the value measured by the temperature-measuring device.

According to the teachings herein, the blood purification apparatus includes the detecting device that is capable of detecting the environmental condition at the time of the hot-water-disinfection process in which the tube is disinfected with hot water or the parameter regarding the environmental condition, and the estimating device that estimates the hot-water-disinfection time required for the hot-water disinfection of the tube in accordance with the environmental condition or the parameter regarding the environmental condition detected by the detecting device. Therefore, the hot-water-disinfection time can be optimized with consideration for the environmental conditions.

According to the teachings herein, the blood purification apparatus further includes the calculating device that calculates, from the hot-water-disinfection time estimated by the estimating device, the completion time of the hot-water disinfection or the remaining time before the completion of the hot-water disinfection. Therefore, the operator can recognize the completion time of the hot-water-disinfection process or the remaining time before the completion of the hot-water-disinfection process.

According to the teachings herein, the blood purification apparatus further includes the circulation tube for forming the circulation flow route that allows the liquid to circulate in the hot-water-disinfection process, the heating device capable of heating the liquid circulating through the circulation flow route and generating hot water at a temperature required for hot-water disinfection, and the temperature-measuring device capable of measuring the temperature of the liquid heated by the heating device. The detecting device is the temperature-measuring device, and the value measured by the temperature-measuring device is the parameter regarding the environmental condition. Therefore, the required hot-water-disinfection time can be estimated by using the temperature-measuring device that is intended for measuring the temperature of the tube during the blood purification treatment.

According to the teachings herein, the heating device and the temperature-measuring device are provided to the circulation flow route. Therefore, the required hot-water-disinfection time can be estimated by using the heating device and the temperature-measuring device.

According to the teachings herein, the temperature-measuring device is provided on the downstream side of the heating device. That is, the temperature-measuring device is provided at a position where the rise of the temperature with the heating by the heating device is quick. Hence, the required hot-water-disinfection time can be estimated more quickly.

According to the teachings herein, the temperature-measuring device is provided on the downstream side of and near the heating device. That is, the temperature-measuring device is provided at a position where the rise of the temperature with the heating by the heating device is quicker. Hence, the required hot-water-disinfection time can be estimated much more quickly.

According to the teachings herein, the estimating device has the table created for obtaining the hot-water-disinfection time from the value measured by the temperature-measuring device. The table is prepared in accordance with the correlation, under a certain environmental condition, between the value measured by the temperature-measuring device and the temperature at the position of the circulation flow route that is on the downstream side of the temperature-measuring device and on the upstream side of the heating device (or on the upstream side of and near the heating device) (or the temperature at the position of the circulation flow route where the rise of the temperature with the heating by the heating device is slow). Therefore, the required hot-water-disinfection time can be estimated more precisely and more smoothly.

According to the teachings herein, at least one of the environmental conditions summarized in the table is identifiable from the value measured by the temperature-measuring device. That is, the estimation can be made without the consideration for the other environmental conditions summarized in the table. Therefore, the required hot-water-disinfection time can be estimated more precisely and more quickly.

BRIEF DESCRIPTION OF THE DRAWINGS

FIG. 1 is a schematic diagram illustrating a blood purification apparatus according to an embodiment of the present teachings (with a blood circuit connected thereto).

FIG. 2 is a perspective view illustrating the appearance of a dialysis-apparatus body included in the blood purification apparatus.

FIG. 3 is a schematic diagram illustrating the blood purification apparatus (when a hot-water-disinfection process is performed).

FIG. 4 is a schematic diagram illustrating a table stored in an estimating device included in the blood purification apparatus.

FIG. 5 is a schematic diagram illustrating items displayed on a monitor screen included in the blood purification apparatus.

FIG. 6 is a schematic diagram illustrating a blood purification apparatus according to another embodiment of the present teachings (in which a thermistor is provided on the upstream side of a heater).

FIG. 7 is a schematic diagram illustrating a blood purification apparatus according to yet another embodiment of the present teachings (in which thermistors are provided on the upstream side and the downstream side, respectively, of the heater).

FIG. 8 is a schematic diagram illustrating a blood purification apparatus according to yet another embodiment of the present teachings (in which thermistors are provided near the distal ends of a dialysate introduction line and a dialysate drain line, respectively).

FIG. 9 is a schematic diagram illustrating a blood purification apparatus according to yet another embodiment of the present teachings (in which a thermistor is provided to a circulation tube).

FIG. 10 is a schematic diagram illustrating a blood purification apparatus according to yet another embodiment of the present teachings (in which a voltmeter is a detecting device).

DETAILED DESCRIPTION

Embodiments of the present teachings will now be described specifically with reference to the drawings.

A blood purification apparatus according to an embodiment is intended for purifying the blood of a patient while extracorporeally circulating the blood and is applied to a hemodialysis apparatus used in hemodialysis treatment. The hemodialysis apparatus basically includes, as illustrated in FIG. 1, a blood circuit 1 (an arterial blood circuit 1a and a venous blood circuit 1b), a dialyzer 2 serving as a blood purification device, a dialysate introduction line L1 connectable to the dialyzer 2 and allowing dialysate to be introduced into the dialyzer 2, a dialysate drain line L2 connectable to the dialyzer 2 and allowing drain liquid from the dialyzer 2 to be discharged, connecting tools C1 and C2 (each being a connecting tool called "coupling"), a control device 10, an estimating device 11, and a calculating device 12.

The blood circuit 1 basically includes the arterial blood circuit 1a and the venous blood circuit 1b that are each made of a flexible tube. The dialyzer 2 is provided between the arterial blood circuit 1a and the venous blood circuit 1b. The arterial blood circuit 1a is provided at the distal end thereof with a connector a to which an arterial puncture needle is connectable, and at a halfway position thereof with a peristaltic blood pump 3. The venous blood circuit 1b is provided at the distal end thereof with a connector b to which a venous puncture needle is connectable, and at a halfway position thereof with an air-trap chamber 4 for bubble removal.

When the blood pump 3 is activated with the arterial puncture needle and the venous puncture needle being stuck in the patient, the blood of the patient flows through the arterial blood circuit 1a into the dialyzer 2, where the blood is purified and ultrafiltered. Then, the blood flows through the venous blood circuit 1b while undergoing bubble removal in the air-trap chamber 4, and returns into the body of the patient. Thus, the blood of the patient can be purified by the dialyzer 2 while being made to extracorporeally circulate through the blood circuit.

The dialyzer 2 has, in a housing thereof, a blood introduction port 2a, a blood delivery port 2b, a dialysate introduction port 2c, and a dialysate delivery port 2d. The proximal end of the arterial blood circuit 1a is connected to the blood introduction port 2a. The proximal end of the venous blood circuit 1b is connected to the blood delivery port 2b. The dialysate introduction port 2c and the dialysate delivery port 2d are connected to the dialysate introduction line L1 and the dialysate drain line L2 with the connecting tools C1 and C2 interposed therebetween, respectively.

The dialyzer 2 houses a plurality of hollow fibers. The hollow fibers each provide a blood flow route thereinside. A space between the outer peripheral surface of each of the hollow fibers and the inner peripheral surface of the housing serves as a dialysate flow route. The hollow fibers each have a number of very small holes (pores) extending therethrough from the outer peripheral surface to the inner peripheral surface, thereby forming hollow fiber membranes. Hence, waste products, excessive water, and the like contained in the blood are allowed to penetrate through the membranes into the dialysate.

The dialysate introduction line L1 and the dialysate drain line L2 are connected to a duplex pump 5 that delivers the dialysate prepared to have a predetermined concentration to the dialyzer 2 and discharges waste products and the like together with the dialysate from the dialyzer 2. Specifically, the duplex pump 5 is provided over the dialysate introduction line L1 and the dialysate drain line L2. When the duplex pump 5 is activated, the dialysate can be introduced into the dialyzer 2 through the dialysate introduction line L1 while being discharged from the dialyzer 2 through the dialysate drain line L2.

The dialysate introduction line L1 is provided with electromagnetic valves V1 and V2 and filtration filter 7. The dialysate to be introduced into the dialyzer 2 can be filtered by the filtration filter 7, and the flow route of the dialysate is closable or openable with an arbitrary timing by the electromagnetic valves V1 and V2. On the other hand, the dialysate drain line L2 is provided with electromagnetic valves V3 and V4. The flow route is closable or openable with an arbitrary timing by the electromagnetic valves V3 and V4.

The dialysate introduction line L1 and the dialysate drain line L2 are each connected to bypass lines L4 and L5 on a side of the duplex pump 5 that is nearer to the dialyzer 2 and on the other side of the duplex pump 5. The bypass lines L4 and L5 are each communicable with the dialysate introduction line L1 and with the dialysate drain line L2. The bypass lines L4 and L5 are provided with electromagnetic valves V5 and V6, respectively, that are capable of opening and closing the respective flow routes. The dialysate drain line L2 is connected to a detour line L3 that detours the duplex pump 5. The detour line L3 is provided with an ultrafiltration pump 6. Hence, when the ultrafiltration pump 6 is activated while the blood of the patient is made to extracorporeally circulate through the blood circuit, ultrafiltration in which water is removed from the blood flowing through the dialyzer 2 can be performed.

The dialysate introduction line L1 and the dialysate drain line L2 according to the present embodiment are provided at the distal ends thereof with the connecting tools C1 and C2, respectively. When the connecting tools C1 and C2 are connected to each other (see FIG. 3), the dialysate introduction line L1 and the dialysate drain line L2 form a closed circuit. When the connecting tools C1 and C2 thus connected are disconnected from each other, the closed circuit is opened, allowing the connecting tools C1 and C2 to be connected to the dialyzer 2 (see FIG. 1).

Referring to FIG. 3, in a hot-water-disinfection process, the bypass line L5 according to the present embodiment serves as a circulation tube for forming a circulation flow route through which liquid (water) can be made to circulate. Specifically, as illustrated in FIG. 3, a circulation flow route for allowing the liquid to circulate therethrough can be formed by connecting the connecting tools C1 and C2 to each other to form a closed circuit, with the electromagnetic valves V1 and V4 being closed and the electromagnetic valve V6 being open (the state is changeable by opening or closing each of the electromagnetic valves V2, V3, and V5 with an arbitrary timing, between a state where the bypass line L4 forms part of the circulation flow route and a state where the flow route on the side having the connecting tools C1 and C2 forms part of the circulation flow route).

The dialysate introduction line L1 is further provided with a heater 8 serving as a heating device and a thermistor 9 serving as a temperature-measuring device between the point of connection thereof to the bypass line L5 (the circulation tube) and the point of connection thereof to the duplex pump 5. When the heater 8 is activated by being powered, the liquid circulating through the circulation flow route formed by the bypass line L5 (the circulation tube) is heated, whereby hot water at a temperature required for hot-water disinfection can be generated. The thermistor 9 is a sensor capable of measuring the temperature of the liquid heated by the heater 8.

As illustrated in FIG. 2, the hemodialysis apparatus according to the present embodiment includes a dialysis-apparatus body H. The dialysis-apparatus body H includes a monitor screen M for displaying information such as settings for the treatment and the patient's condition during the treatment, a syringe pump S, a warning lamp R, and so forth. The dialysis-apparatus body H is provided with the duplex pump 5, the blood pump 3, and the tubes such as the dialysate introduction line L1 and the dialysate drain line L2. Note that the term "tubes" according to the present embodiment include not only the dialysate introduction line L1 for introducing the dialysate into the dialyzer 2 and the dialysate drain line L2 for discharging the drain liquid from the dialyzer 2 but also other tubes through each of which the dialysate or the drain liquid flows.

The control device 10 is a microcomputer or the like provided in the dialysis-apparatus body H and is capable of controlling the opening/closing of the electromagnetic valves (V1 to V6) before, after, and during the treatment, and the operations of actuators provided for the duplex pump 5, the ultrafiltration pump 6, and others. Furthermore, the control device 10 is capable of controlling the heater 8 during the dialysis treatment to heat the dialysate to be introduced into the dialyzer 2 to an appropriate temperature while controlling the thermistor 9 to measure the temperature of the dialysate and controlling the operation of the heater 8.

In particular, at the time of the hot-water-disinfection process in which the tubes are disinfected with hot water, the control device 10 according to the present embodiment controls the opening and closing of the electromagnetic valves (V1 to V6) to form the circulation flow route illustrated in FIG. 3, and activates the heater 8, whereby hot water at a temperature required for hot-water disinfection can be generated. The present embodiment employs the circulation tube (the bypass line L5) for forming, at the time of the hot-water-disinfection process, the circulation flow route that allows the liquid to circulate therethrough, the heating device (the heater 8) capable of heating the liquid circulating through the circulation flow route and thus generating hot water at a temperature required for hot-water disinfection, and the temperature-measuring device (the thermistor 9) capable of measuring the temperature of the liquid heated by the heating device. Hence, the temperature of the liquid heated by the heater 8 while being made to circulate through the circulation flow route can be measured in real time by the thermistor 9.

The blood purification apparatus according to the present embodiment includes the detecting device (the thermistor 9) that is capable of detecting environmental conditions at the time of the hot-water-disinfection process, in which the tubes provided in the dialysis-apparatus body H are disinfected with hot water, or parameter regarding the environmental conditions; the estimating device 11 that estimates the hot-water-disinfection time required for the hot-water disinfection of the tubes in accordance with the environmental conditions or the parameter regarding the environmental conditions detected by the detecting device; and the calculating device 12 that calculates the completion time of the hot-water disinfection from the hot-water-disinfection time estimated by the estimating device 11.

The environmental conditions at the time of the hot-water-disinfection process refer to conditions for generating hot water at a temperature required for hot-water disinfection performed by heating the liquid in the tubes (the circulation flow route in the present embodiment) by using the heater 8 (the heating device). For example, the followings can be named: the power-source voltage (the input voltage of the heater 8), the supply water temperature (the temperature of water to be introduced from the dialysate introduction line L1), the ambient temperature (the temperature around the dialysis-apparatus body H), and so forth. The parameter regarding the environmental conditions refer to any parameter directly or indirectly affected by the above environmental conditions. For example, the followings can be named: the value measured by the thermistor 9 (the temperature-measuring device), the thermal capacity of the heater 8, the capacity of the tubes, the individual differences among components provided to the tubes (the difference in pressure loss, the state of fitting of assembled components, etc.), and so forth.

The detecting device according to the present embodiment is the thermistor 9 (the temperature-measuring device) capable of measuring the temperature of the liquid in a tube (the water introduced into the dialysate introduction line L1) that is heated by the heater 8 (the heating device). The detecting device is capable of detecting the temperature of the liquid heated by the heater 8, the temperature being a parameter affected by the environmental conditions. That is, according to the present embodiment, the detecting device corresponds to the thermistor 9 (the temperature-measuring device), and the value measured by the thermistor 9 corresponds to the parameter regarding the environmental conditions. Furthermore, the thermistor 9 according to the present embodiment is provided on the downstream side of the heater 8 (specifically, a position on the downstream side of and near the heater 8), so that changes in the temperature (the rise of the temperature) of the liquid heated by the heater 8 can be detected immediately.

The estimating device 11 is a microcomputer or the like provided in the dialysis-apparatus body H and is configured to estimate the hot-water-disinfection time required for the hot-water disinfection of the tube in accordance with the value measured by the thermistor 9 (the parameter regarding the environmental conditions). Specifically, as summarized in FIG. 4, the estimating device 11 according to the present embodiment has a table for obtaining the hot-water-disinfection time from the value measured by the thermistor 9. The table is prepared in accordance with the correlation, under certain environmental conditions, between the value measured by the thermistor 9 (the temperature-measuring device) and the temperature at a position of the circulation flow route that is on the downstream side of the thermistor 9 and on the upstream side of the heater 8 (the heating device), or preferably a position of the circulation flow route that is on the downstream side of the thermistor 9 and on the upstream side of and near the heater 8 (the heating device), or more preferably a position of the circulation flow route where the rise of the temperature with the heating by the heater 8 (the heating device) is slow, or particularly preferably a position of the circulation flow route where the rise of the temperature with the heating by the heater 8 (the heating device) is slowest.

The above table is obtained from an experiment or the like conducted in advance with the blood purification apparatus to be used. In the experiment, the environmental conditions, which are the power-source voltage (the input voltage of the heater 8); the supply water temperature; and the ambient temperature, are each changed to any value between the upper limit and the lower limit, and the temperature (the time elapsed before the temperature rises to a predetermined temperature X° C., the degree of temperature rise in X minutes, or the like) is measured by the thermistor 9 under each of different sets of environmental conditions. Meanwhile, the following correlation is acquired in advance through an experiment or the like: the correlation, under each of the different sets of environmental conditions, between the value measured by the thermistor 9 (the time elapsed before the temperature rises to a predetermined temperature X° C., the degree of temperature rise in X minutes, or the like) and the temperature at a position of the circulation flow route that is on the downstream side of the thermistor 9 and on the upstream side of the heater 8, or preferably a position of the circulation flow route that is on the downstream side of the thermistor 9 and on the upstream side of and near the heater 8, or more preferably a position of the tube forming the circulation flow route where the rise of the temperature is slow (hereinafter, this position (referred to as the estimation position) is taken as a representative example, and examples of the estimation position that can be assumed include a position on the upstream side of and near the heater 8, a position of the bypass line L5 forming the circulation flow route, and a position of a line branching off from the dialysate introduction line L1 or the dialysate drain line L2), or particularly preferably a position of the tube forming the circulation flow route where the rise of the temperature is slowest.

Thus, the relationship between the rise of the temperature measured by the thermistor 9 and the time period with which the required disinfection effect is guaranteed at the estimation position can be obtained, and the washing-disinfection time (the hot-water-disinfection time) can be obtained therefrom. The table created from the values measured by the thermistor 9 under the respective sets of conditions as described above (changes in the temperature) and the values of the washing-disinfection time (the hot-water-disinfection time) corresponding thereto is stored in the estimating device 11. Thus, at the time of the hot-water-disinfection process, the hot-water-disinfection time required for the hot-water disinfection under the set of environmental conditions at that time can be estimated from the value measured by the thermistor 9.

The hot-water-disinfection time estimated as described above is displayed, as illustrated in FIG. 5, on the monitor screen M included in the blood purification apparatus and is notified to a medical staff therearound. Specifically, the monitor screen M displays various pieces of information required, including a display part M1 in which the sum of the hot-water-disinfection time and the required washing time (the time period for washing with washing water) is displayed, a display part M2 in which the hot-water-disinfection time and the required washing time are displayed, and a remaining time M3 before the completion of the hot-water disinfection. According to the present embodiment, the calculating device 12 is capable of calculating the completion time of hot-water disinfection (the point of time after the elapse of the hot-water-disinfection time from the present time) from the hot-water-disinfection time estimated by the estimating device 11. Therefore, the completion time may also be displayed on the monitor screen M.

The present embodiment concerns a case where a parameter regarding environmental conditions is detected by the thermistor 9 (the temperature-measuring device). Alternatively, another detecting device that is capable of directly detecting environmental conditions (such as the input voltage of the heater 8, the supply water temperature, and the ambient temperature) or yet another detecting device that is capable of detecting another parameter regarding such environmental conditions may be employed. Moreover, instead of or in addition to the input voltage of the heater 8, the supply water temperature, and the ambient temperature, other conditions may be detected.

The above embodiment employs the detecting device (the thermistor 9) that is capable of detecting environmental conditions at the time of the hot-water-disinfection process in which a tube is disinfected with hot water or a parameter regarding the environmental conditions, and the estimating device 11 that estimates the hot-water-disinfection time required for the hot-water disinfection of the tube (the optimum hot-water-disinfection time that guarantees the disinfection effect) from the environmental conditions or the parameter regarding the environmental conditions detected by the detecting device. Therefore, the hot-water-disinfection time can be optimized with consideration for the environmental conditions. The above embodiment further employs the calculating device 12 that calculates the completion time of the hot-water disinfection or the remaining time before the completion of the hot-water disinfection from the hot-water-disinfection time estimated by the estimating device 11. Therefore, if the apparatus is configured to display the result of this calculation, the operator can recognize the completion time of the hot-water-disinfection process.

The above embodiment further employs the circulation tube for forming the circulation flow route that allows liquid to circulate in the hot-water-disinfection process, the heater 8 (the heating device) capable of heating the liquid that circulates through the circulation flow route and generating hot water that is at a temperature required for hot-water disinfection, and the thermistor 9 (the temperature-measuring device) capable of measuring the temperature of the liquid heated by the heater 8. The detecting device corresponds to the thermistor 9 (the temperature-measuring device). The value measured by the thermistor 9 is taken as a parameter regarding the environmental conditions. Therefore, the required hot-water-disinfection time can be estimated by using the thermistor 9 that is intended for measuring the temperature of the tube during the blood purification treatment. Note that the required hot-water-disinfection time can be estimated by using the heater 8 (the heating device) and the thermistor 9 (the temperature-measuring device) because the heater 8 and the thermistor 9 are provided to the circulation flow route.

The estimating device 11 according to the present embodiment has the table for obtaining the hot-water-disinfection time from the value measured by the thermistor 9, and the table is prepared in accordance with the correlation, under certain environmental conditions, between the value measured by the temperature-measuring device and the temperature at the position of the circulation flow route where the rise of the temperature with the heating by the heater 8 (the heating device) is slowest. Therefore, the required hot-water-disinfection time can be estimated more precisely and more smoothly. In particular, the thermistor 9

(the temperature-measuring device) according to the present embodiment is provided on the downstream side of the heater 8 (the heating device) (particularly, on the downstream side of and near the heater 8). That is, the thermistor 9 is provided at a position where the rise of the temperature with the heating by the heater 8 is quick. Hence, the required hot-water-disinfection time can be estimated more quickly.

At least one of the sets of environmental conditions summarized in the table stored in the estimating device 11 may be identified from the value measured by the thermistor 9 (the temperature-measuring device). For example, as illustrated in FIG. 6, if the thermistor 9 is provided at a position of the dialysate introduction line L1 that is on the upstream side of and near the heater 8, the supply water temperature among the environmental conditions can be identified. Alternatively, as illustrated in FIG. 7, if the thermistor 9 (the temperature-measuring device) is provided at each of a position on the upstream side of and near the heater 8 and a position on the downstream side of and near the heater 8, the input voltage of the heater 8 and the supply water temperature among the environmental conditions can be estimated and identified. Alternatively, as illustrated in FIG. 8, if the thermistor 9 is provided at each of a position of the dialysate introduction line L1 that is near the distal end thereof and a position of the dialysate drain line L2 that is near the distal end thereof (on the side where the connecting tools C1 and C2 are connected to each other), the ambient temperature among the environmental conditions can be identified. As described above, if at least one of the environmental conditions summarized in the table can be identified from the value measured by the thermistor 9 (the temperature-measuring device), the estimation can be made without the consideration for the other environmental conditions summarized in the table (the estimation can be made from the identified environmental condition). Therefore, the required hot-water-disinfection time can be estimated more precisely and more quickly.

While blood purification apparatuses according to some embodiments has been described above, the present teachings is not limited thereto. The thermistor 9 serving as the temperature-measuring device may be provided at any other position of the circulation flow route. For example, as illustrated in FIG. 9, the thermistor 9 may be provided to the bypass line L5 (the circulation tube), and the hot-water-disinfection time required for the hot-water disinfection of the tube may be estimated by the estimating device 11 from the value measured by the thermistor 9.

Alternatively, as illustrated in FIG. 10, a voltmeter 13 capable of directly measuring the input voltage of the heater 8 may be employed. In such a case, the value measured by the voltmeter 13 may be detected as one of the environmental conditions, and the hot-water-disinfection time required for the hot-water disinfection of the tube may be estimated by the estimating device 11 from the measured value. Moreover, another parameter (such as changes in the input control value (the operating ratio) of the heater 8 or the like) instead of the temperature measured by the thermistor 9 (the temperature-measuring device) or the voltage measured by the voltmeter 13 may be taken as a parameter regarding the environmental conditions. Specifically, the pressure of the liquid flowing in the tube, or any other parameter may be taken.

Instead of the blood purification apparatus included in a central system as described in the above embodiment, a personal dialysis apparatus (an apparatus capable of performing dialysis treatment with a dialysate at a predetermined concentration that is prepared by mixing undiluted dialysate and clean water together in a dialysis-apparatus body) is also acceptable. On the other hand, the timing with which the estimating device 11 estimates the hot-water-disinfection time required for hot-water disinfection is not limited to a point at the time of the hot-water-disinfection process. The estimation may be performed at the time of, for example, a dialysate-washing process (a washing process) performed before the hot-water-disinfection process, or at the time of a process of self-diagnosis of the tube (that is, the hot-water-disinfection time may be estimated before the hot-water-disinfection process is started). Moreover, the parameter, such as the temperature, used by the estimating device 11 may also be used for the diagnosis of any abnormality of the tube, any malfunction of the heater 8, or the like.

The blood purification apparatus may have any additional functions, as long as the apparatus includes a detecting device that is capable of detecting environmental conditions at the time of the hot-water-disinfection process in which a tube is disinfected with hot water, or a parameter regarding the environmental conditions, and an estimating device that estimates the hot-water-disinfection time required for the hot-water-disinfection of a tube in accordance with the environmental conditions or the parameter regarding the environmental conditions detected by the detecting device.

REFERENCE SIGN LIST

1 blood circuit
2 dialyzer (blood purification device)
3 blood pump
4 air-trap chamber
5 duplex pump
6 ultrafiltration pump
7 filtration filter
8 heater (heating device)
9 thermistor (temperature-measuring device)
10 control device
11 estimating device
12 calculating device
13 voltmeter
L1 dialysate introduction line (tube)
L2 dialysate drain line (tube)
L5 bypass line (circulation tube)

The invention claimed is:

1. A blood purification apparatus provided with a blood purification device for giving dialysis treatment to a patient, and with a tube for introducing dialysate into or discharging drain liquid from the blood purification device, the blood purification apparatus comprising:

a first detecting device that detects an environmental condition at a time of a hot-water-disinfection process in which the tube is disinfected with hot water or a parameter regarding the environmental condition, and a second detecting device that measures a temperature of liquid heated by a heating device downstream of the heating device; and an estimating device that estimates a hot-water-disinfection time required for the hot-water disinfection of the tube in accordance with the environmental condition or the parameter regarding the environmental condition detected by the first detecting device;

a calculating device that calculates from the hot-water disinfection time estimated by the estimating device, a completion time of the hot-water disinfection or a remaining time before the completion of the hot water disinfection;

a control device that controls the first detecting device and the second detecting device; and wherein the environmental condition includes power-source voltage, supply water temperature upstream of the heating device, and ambient temperature.

2. The blood purification apparatus according to claim 1, further comprising:

a circulation tube for forming a circulation flow route that allows liquid to circulate in the hot-water-disinfection process;

a heating device capable of heating the liquid circulating through the circulation flow route and generating hot water at a temperature required for hot-water disinfection; and wherein the temperature-measuring device measures a temperature of the liquid heated by the heating device, wherein the first detecting device includes a temperature-measuring device, and a value measured by the temperature-measuring device is the parameter regarding the environmental condition.

3. The blood purification apparatus according to claim 2, wherein the heating device and the temperature-measuring device are provided to the circulation flow route.

4. The blood purification apparatus according to claim 3, wherein the temperature-measuring device is provided on a downstream side of the heating device.

5. The blood purification apparatus according to claim 4, wherein the temperature-measuring device is provided on the downstream side of and near the heating device.

6. The blood purification apparatus according to claim 3, wherein a table is stored in the estimating device and the table estimates the hot-water-disinfection time from the value measured by the temperature-measuring device, the table being prepared in accordance with a correlation, under a certain environmental condition, between the value measured by the temperature-measuring device and a temperature at a position of the circulation flow route that is on a downstream side of the temperature-measuring device and on the upstream side of the heating device.

7. The blood purification apparatus according to claim 3, wherein a table is stored in the estimating device and the table estimates the hot-water-disinfection time from the value measured by the temperature-measuring device, the table being prepared in accordance with a correlation, under a certain environmental condition, between the value measured by the temperature-measuring device and a temperature at a position of the circulation flow route that is on a downstream side of the temperature-measuring device and on the upstream side of and near the heating device.

8. The blood purification apparatus according to claim 3, wherein a table is stored in the estimating device and the table estimates the hot-water-disinfection time from the value measured by the temperature-measuring device, the table being prepared in accordance with a correlation, under a certain environmental condition, between the value measured by the temperature-measuring device and a temperature at a position of the circulation flow route where a rise of the temperature with the heating by the heating device is slow.

9. The blood purification apparatus according to claim 6, wherein at least one of the environmental conditions summarized in the table is identifiable from the value measured by the temperature-measuring device.

10. The blood purification apparatus according to claim 1, wherein the blood purification apparatus includes an introduction line and a dialysate drain line and a connecting tool located at a distal end of the introduction line and a distal end of the dialysate drain line, and the connecting tools connect the introduction line to the dialysate drain line so that a closed circuit is formed and connect to a dialyzer so that the blood purification apparatus is connected to a blood circuit.

11. The blood purification apparatus according to claim 1, wherein the estimating device includes a microcomputer.

12. The blood purification apparatus according to claim 2, wherein the temperature-measuring device is a thermistor.

13. The blood purification apparatus according to claim 1, wherein the tubes include an introduction line having a distal end, a dialysate drain line having a distal end, a connecting tool on the distal end of the introduction line, a connecting tool on the distal end of the dialysate drain line, a temperature-measuring device is located near the distal end of the of the introduction line and the connecting tool, and the temperature-measuring device is located near the distal end of the dialysate drain line and the connecting tool.

14. A blood purification apparatus provided with a blood purification device for giving dialysis treatment to a patient, and with a tube for introducing dialysate into or discharging drain liquid from the blood purification device, the blood purification apparatus comprising:

a detecting device that detects an environmental condition at a time of a hot-water-disinfection process in which the tube is disinfected with hot water or a parameter regarding the environmental condition;

an estimating device that estimates a hot-water-disinfection time required for the hot-water disinfection of the tube in accordance with the environmental condition or the parameter regarding the environmental condition detected by the detecting device;

a calculating device that calculates from the hot-water disinfection time estimated by the estimating device, a completion time of the hot-water disinfection or a remaining time before the completion of the hot water disinfection;

a control device that controls the detecting device; and wherein the environmental condition is power-source voltage, and supply water temperature, or ambient temperature; and wherein the blood purification apparatus includes a voltmeter that directly measures the power-source voltage of the heater.

15. The blood purification apparatus of claim 14, wherein one of the environmental conditions is a pressure of a liquid flowing into the tube.

16. The blood purification apparatus of claim 14, wherein an introduction line and the dialysate drain line are each connected to a bypass line.

17. The blood purification apparatus of claim 16, wherein the bypass line forms a circulation flow route that liquid is circulated through during the hot-water disinfection process.

18. The blood purification apparatus of claim 17, wherein the liquid in the circulation flow route is heated by the heater to a temperature required for hot-water disinfection.

19. The blood purification apparatus of claim 1, wherein the completion time or the remaining time before the completion of the hot-water disinfection, is calculated based on the hot-water disinfection time estimated by the estimating device.

* * * * *